United States Patent
Kelly et al.

(10) Patent No.: US 6,325,622 B1
(45) Date of Patent: Dec. 4, 2001

(54) ORTHODONTIC BRACKET AND LATCH ASSEMBLY

(75) Inventors: John S. Kelly, Arcadia; Joseph M. Caruso, Redlands, both of CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/330,695

(22) Filed: Jun. 11, 1999

(51) Int. Cl.[7] .................................................. A61C 7/00
(52) U.S. Cl. .................................................. 433/11; 433/10
(58) Field of Search .................................. 433/10, 11, 8, 433/9

(56) References Cited

U.S. PATENT DOCUMENTS

| | | | |
|---|---|---|---|
| 3,772,787 | 11/1973 | Hanson | 32/14 |
| 4,103,423 | 8/1978 | Kessel | 32/14 |
| 4,149,314 | 4/1979 | Nonnenmann | 32/14 |
| 4,197,642 | 4/1980 | Wallshein | 433/11 |
| 4,248,588 | 2/1981 | Hanson | 433/11 |
| 4,260,375 | 4/1981 | Wallshein | 433/11 |
| 4,371,337 | 2/1983 | Pletcher | 433/10 |
| 4,492,573 | 1/1985 | Hanson | 433/11 |
| 4,531,911 | 7/1985 | Creekmore | 433/8 |
| 4,559,012 | 12/1985 | Pletcher | 433/10 |
| 4,712,999 | 12/1987 | Rosenberg | 433/8 |
| 4,725,229 | 2/1988 | Miller | 433/11 |
| 5,094,614 | 3/1992 | Wildman | 433/14 |
| 5,269,681 | 12/1993 | Degnan | 433/11 |
| 5,322,435 | 6/1994 | Pletcher | 433/11 |
| 5,516,284 | 5/1996 | Wildman | 433/10 |
| 5,613,850 | 3/1997 | Wildman et al. | 433/10 |
| 5,630,716 | * 5/1997 | Hanson | 433/14 |
| 5,681,165 | 10/1997 | Feldman | 433/8 |
| 5,685,711 | 11/1997 | Hanson | 433/11 |
| 5,711,666 | 1/1998 | Hanson | 433/11 |
| 5,857,850 | 1/1999 | Voudouris | 433/11 |
| 5,906,486 | * 5/1999 | Hanson | 433/11 |
| 6,042,374 | 3/2000 | Farzin-Nia et al. . | |

FOREIGN PATENT DOCUMENTS 04166147   12/1992   (JP) .
WO98/20805   5/1998   (WO) .

* cited by examiner

*Primary Examiner*—Ralph A. Lewis
(74) *Attorney, Agent, or Firm*—James D. Christoff (57) ABSTRACT

An orthodontic bracket assembly includes a bracket and latch coupled to the bracket. The latch is movable between a slot-open position to enable removal or insertion of an archwire in an archwire slot of the bracket, and a slot-closed position to retain the archwire in the archwire slot. The latch includes a first portion that is received in a passage that extends in a generally occlusal-gingival direction through a body of the bracket, and a second portion that is received lingually of at least one bracket tiewing when the latch is in the slot-closed position.

39 Claims, 8 Drawing Sheets

ORTHODONTIC BRACKET AND LATCH ASSEMBLY

BACKGROUND OF THE INVENTION

1. Field of the Invention

The present invention broadly relates to brackets and ligatures used in orthodontic treatment. More specifically, the present invention relates to an assembly of an orthodontic bracket and a latch for releasably retaining an archwire in an archwire slot of the bracket.

2. Description of the Related Art

Orthodontic therapy is a specialized type of treatment within the field of dentistry, and involves movement of malpositioned teeth to orthodontically correct locations. Orthodontic treatment often improves the patient's occlusion and typically enhances the aesthetic appearance of the teeth.

Many types of orthodontic treatment programs involve the use of a set of tiny appliances and wires that are commonly known collectively as "braces". During such treatment programs, small appliances known as brackets are fixed to the patient's anterior, cuspid and bicuspid teeth, and an archwire is inserted into a slot of each bracket. The archwire forms a track to guide movement of the teeth to orthodontically correct locations. End sections of the archwires are typically captured in tiny appliances known as buccal tubes that are fixed to the patient's molar teeth.

Orthodontists often use ligatures to connect the archwire to the brackets and to urge the archwire into an orientation of seating engagement in the archwire slot. One type of commercially available orthodontic ligature is a small, elastomeric O-ring. Orthodontic O-rings are installed by stretching the O-ring around small wings (known as "tiewings") that are connected to the bracket body on the gingival side (i.e., the side closest to the patient's gingiva or gums) and on the occlusal side (i.e., the side closest to the outer tips of the teeth) of the archwire slot. Once installed, the O-ring ligature extends around the tiewings as well as over the labial side of the archwire (i.e., the side closest to the patient's lips or cheeks) and urges the archwire toward a lingual wall (i.e., the wall closest to the patient's tongue) of the archwire slot.

Metal ligatures, such as ligatures made of stainless steel, are also used to retain archwires in archwire slots of brackets. Metal ligatures are typically made of a short section of initially straight wire. During installation, the wire ligature is hooked around the tiewings and extended over the labial side of the archwire, and end sections of the ligature are then twisted together to form a loop to retain the ligature in place.

Unfortunately, some orthodontists are not entirely satisfied with conventional elastomeric and metal ligatures. Such ligatures are somewhat time-consuming to install, both during initial installation and also during reinstallation whenever replacement of the archwire or ligatures is desired. As can be appreciated, a savings in the amount of time needed for ligation can help to reduce the total time that the practitioner must spend with the patient and consequently aid in reducing the overall costs of orthodontic treatment.

Other disadvantages are also associated with elastomeric and metal ligatures. For example, there have been reports that certain polyurethane elastomeric ligatures have exhibited deformation and force decay during the course of treatment. In some instances, elastomeric ligatures are stained by food and beverages consumed by the patient and become somewhat unsightly. Metal ligatures often have sharp ends that may retain plaque and food debris and also may increase the risk of infection.

In an effort to overcome the problems associated with conventional ligatures, a variety of orthodontic brackets have been proposed having various types of latches for coupling the archwire to the bracket. Such brackets are also known as self-ligating brackets. The latch comprises a clip, spring member, cover, shutter, bail or other structure that is connected to the bracket body for retaining an archwire in the archwire slot.

Examples of self-ligating orthodontic brackets having generally U-shaped ligating latch clips are described in U.S. Pat. Nos. 3,772,787, 4,248,588 and 4,492,573. In general, the clip of such brackets is slidably mounted on the bracket body, and a dental explorer or other small-tipped dental tool is used to move the clip relative to the body when needed in order to open or close the archwire slot. A self-ligating bracket known as the "Speed" brand bracket also has a movable, generally U-shaped clip for ligating the archwire to the bracket.

Other types of self-ligating brackets have latches that resemble swinging shutters or closures that pivotally move between a slot-open and a slot-closed position. For example, U.S. Pat. No. 4,712,999 has a rotatable cover plate that is pivotally connected at one end to a tiewing of the bracket along one side of the slot, and is releasably engagable at the other end with a tiewing that is located along the opposite side of the archwire slot. Other orthodontic brackets with swinging latches are described in U.S. Pat. Nos. 4,103,423, 5,516,284 and 5,685,711.

U.S. Pat. Nos. 4,371,337 and 4,559,012 describe self-ligating orthodontic brackets having latches that rotate about the longitudinal axis of the archwire slot. The latch of these references has a somewhat cylindrical shape and is rotatably received in a mating, cylindrical channel, and an outwardly extending arm is provided to assist in rotatably moving the latch between a slot-open and a slot-closed position.

A self-ligating orthodontic bracket that is described in U.S. Pat. No. 5,711,666 has a ligating latch that comprises a flexible flat spring member. One end of the spring member is fixed to the bracket body on one side of the archwire slot, and the opposite end of the spring member has notches that releasably engage latch sears or catches when the spring member is moved to a slot-closed position. To open the slot, the notches are disengaged from the catches and the spring member is bent to an orientation sufficient to enable the archwire to be removed from the archwire slot.

Other types of self-ligating orthodontic brackets have latches that comprise essentially flat plates that are slidable between a slot-open and a slot-closed position. Examples of such construction are shown in U.S. Pat. Nos. 5,094,614, 5,322,435 and 5,613,850. In general, the sliding latches described in those references move in upright channels that are located buccolabially of the archwire slot.

Another type of self-ligating bracket that has been proposed in the past has a latch that is made of a section of wire material that functions similar to a bail. The orthodontic brackets described in U.S. Pat. Nos. 4,149,314, 4,725,229 and 5,269,681 have wire-like latches that swing between a slot-closed position and a slot-open position. The orthodontic brackets described in U.S. Pat. Nos. 4,197,642 and 4,260,375 have a wire latch that is slidable between a slot-open and a slot-closed position.

Many practitioners prefer self-ligating orthodontic brackets over brackets that are not self-ligating because handling of an initially separate elastomeric O-ring or a metal ligature wire can be avoided. However, certain types of conventional self-ligating orthodontic brackets are not entirely satisfactory because the costs of manufacture are relatively high. The relatively high manufacturing costs are due, in part, to the fact that many of the components of conventional self-ligating brackets are of a specialized nature and have no other use or function. As a result, lower costs or discounts that are often associated with larger volumes of production are not obtained.

Another problem often associated with conventional self-ligating brackets relates to the general lack of treatment options often afforded by such brackets. For example, the orthodontist may change treatment techniques during the course of treatment and determine that a hook should be connected to a certain bracket. Alternatively, the orthodontist may determine that a particular bracket should provide increased rotational force on the associated tooth in order to better move the tooth to its intended location. Unfortunately, hooks and ligatures providing rotational forces cannot be connected to many conventional self-ligating brackets and, under those circumstances, the orthodontist may debond the self-ligating bracket originally installed and replace it with another bracket that provides such features. As can be appreciated, such removal and replacement of a bracket during the course of treatment represents a time-consuming and costly nuisance for both the practitioner as well as for the patient.

There is a clear need in the art for an orthodontic bracket that provides the features and functions of conventional self-ligating brackets and yet provides, when desired, the features and functions of conventional brackets that are not self-ligating. In this manner, the practitioner can carry out a variety of treatment options using well known and familiar techniques. Moreover, it would be a clear advantage if such a bracket were relatively inexpensive to manufacture in comparison to conventional self-ligating brackets.

SUMMARY OF THE INVENTION

The present invention relates to an orthodontic bracket and latch assembly. A portion of the latch fits within an occlusal-gingival passage of the bracket, such as the "vertical" channel provided in many conventional orthodontic brackets. As such, the assembly may be manufactured at relatively low cost since the bracket of the assembly is optionally identical to or closely similar to existing brackets.

Preferably, the latch is releasably retained in the channel and can be readily removed or installed by the practitioner when desired. For example, the practitioner may elect to remove the latch at some point during the course of treatment in order to use the passage to receive a hook or other auxiliary component. Once the latch is removed, the bracket can be ligated in conventional fashion using an elastomeric O-ring or a wire strand ligature. Additionally, the latch of the invention can be installed on the bracket at any convenient time by the practitioner, such as when the hook or other auxiliary is no longer needed.

In more detail, the present invention concerns in one aspect an orthodontic bracket assembly comprising an orthodontic bracket having a base, a body extending from the base and an archwire slot extending in a generally mesial-distal direction. The bracket also includes at least one gingival tiewing, at least one occlusal tiewing and a passage extending in a generally occlusal-gingival direction. The assembly also includes a latch having a first portion and a second portion. The second portion is movable between a slot-closed position for retaining an archwire in the archwire slot and a slot-open position for removal or insertion of an archwire in the archwire slot. The second portion extends lingually of at least one of the tiewings when the second portion is in the slot-closed position. The first portion is received in the passage.

Another aspect of the present invention also concerns an orthodontic bracket assembly. In this aspect, the assembly includes an orthodontic bracket having a base, a body extending from the base and an archwire slot extending in a generally mesial-distal direction. The bracket also includes a mesial-gingival tiewing, a mesial-occlusal tiewing, a distal-gingival tiewing and a distal-occlusal tiewing. The bracket has a passage extending along a generally occlusal-gingival reference axis. The assembly also includes a wire ligature having a first portion, a second portion and a third portion. The second portion is located between the first portion and the third portion in directions along the length of the ligature. The second portion is movable between a slot-closed position for retaining an archwire in the archwire slot and a slot-open position for removal or insertion of an archwire in the archwire slot. The second portion extends lingually past each of the tiewings when the second portion is in the slot-closed position. The first portion and the third portion are received in the passage.

An additional aspect of the present invention also concerns an orthodontic bracket assembly. In this aspect, the assembly includes an orthodontic bracket having a base, a body extending from the base and an archwire slot extending in a generally mesial-distal direction. The bracket also includes at least one gingival tiewing and at least one occlusal tiewing. Each occlusal tiewing has an outer end section facing in a generally occlusal direction. Each gingival tiewing has an outer end section facing in a generally gingival direction. A latch has a first portion and a second portion, and the first portion is coupled to the body. The second portion is movable between a slot-closed position for retaining an archwire in the archwire slot and a slot-open position for removal or insertion of an archwire in the archwire slot. The second portion extends lingually past each of the tiewings when the second portion is in the slot-closed position. The second portion rests on the outer end section of at least one tiewing when the second portion is in the slot-open position in order to help retain the second portion in the slot-open position.

These and other aspects and features of the invention are described in more detail below and are illustrated in the accompanying drawings.

DETAILED DESCRIPTION OF THE PREFERRED EMBODIMENTS

An orthodontic bracket assembly according to one embodiment of the invention is illustrated in FIGS. 1–10 and is broadly designated by the numeral 20. The assembly 20 includes an orthodontic bracket 22 and a latch or ligature 24 that is coupled to the bracket 22. Preferably, the ligature 24 is releasably coupled to the bracket 22.

The bracket 22 includes a base 26 that is preferably adapted for direct bonding to an outer surface of a tooth. The base 26 preferably has a compound contour that matches the convex shape of the tooth. Optionally, the base 26 is provided with a series of projections that enhance bonding of the bracket 22 to the tooth. As further options, the base 26 may be provided with wire mesh, particulates, grooves, undercuts, adhesive-promoting coatings or any combination thereof in order to enhance bonding.

The bracket 22 also includes a body 28 that extends outwardly from the base 26 in a buccolabial direction (i.e., in a direction toward the patient's lips or cheeks). The body 28 has an occlusal side and a gingival side and may be integral with or initially separate from the base 26. An archwire slot 30 extends through the body 28 and follows a path that extends generally along a mesial (i.e., in a direction toward the middle of the patient's dental arch) and distal (i.e., in a direction away from the middle of the patient's dental arch) reference axis. The archwire slot 30 is identified by the numeral 30 only in FIGS. 1 and 2.

In the illustrated embodiment, the bracket 22 is a "twin tiewing" bracket, having a pair of spaced apart occlusal tiewings (i.e., tiewings that extend toward the outer tips of the patient's teeth) located occlusally of the occlusal side and a pair of spaced apart gingival tiewings (i.e., tiewings that extend toward the patient's gums or gingiva) located gingivally of the gingival side. More particularly, the bracket 22 has a mesial-occlusal tiewing 32, a distal-occlusal tiewing 34, a mesial-gingival tiewing 36 and a distal-gingival tiewing 38. Each of the tiewings 32, 34, 36, 38 is integrally connected to the body 28.

A passage 40 extends through the body 28 along a generally occlusal-gingival reference axis. Preferably, the passage 40 is spaced in a lingual direction (i.e., in a direction toward the patient's tongue) from a lingual side of the archwire slot 30. Moreover, the passage 40 is preferably centrally located in the body 28, such that it extends along a path that is midway between the mesial tiewings 32, 36 and the distal tiewings 34, 38.

In the embodiment shown in FIGS. 1–10, the bracket 22 is considered a "non-angulated" bracket because the tiewings 32, 34, 36, 38 extend in directions perpendicular to the longitudinal, central axis of the archwire slot 30. However, as an alternative, the bracket 22 may be an "angulated" bracket where the tiewings 32, 34, 36, 38 extend in directions parallel to each other but at an angle other than 90° relative to the longitudinal axis of the archwire slot 30. Preferably, the tiewings 32, 34, 36, 38 extend in directions parallel to the long axis of the tooth on which bracket 22 is mounted when the archwire slot 30 is oriented in a direction parallel to the patient's occlusal plane. The passage 40 preferably extends in parallel relationship to the direction of extension of the tiewings 32, 34, 36, 38.

Preferably, the body 28 includes a pair of wall sections 42 (numbered only in FIG. 7) that extend at an angle relative to the central axis of the passage 40. The wall sections 42 converge toward each other as the passage 40 is approached, and provide a somewhat funnel-shaped entrance leading to the passage 40. The angle of convergence can be observed by reference to the dashed lines in FIG. 5.

The ligature 24 has a first portion 44, a second portion 46 and a third portion 48. The second portion 46 is located between the first portion 44 and the third portion 48 in directions along the length of the ligature 24 (i.e., if the ligature 24 were hypothetically pulled to a straight configuration unlike its configuration shown in the drawings). The second portion 46 is connected to the first portion 44 adjacent the gingival side of the body 28. The second portion 46 generally has a shape of an open loop with formed mesial and distal bent segments 50 (numbered only in FIG. 1) that appear when the ligature 24 assumes its normal or relaxed configuration. Preferably, the second portion 46 also includes a pair of occlusal-most bent segments 52 and gingival-most bent segments 54 that also typically appear only when the ligature 24 assumes its normal, relaxed configuration (the bent segments 52, 54 are also only numbered in FIG. 1).

Figure 1:
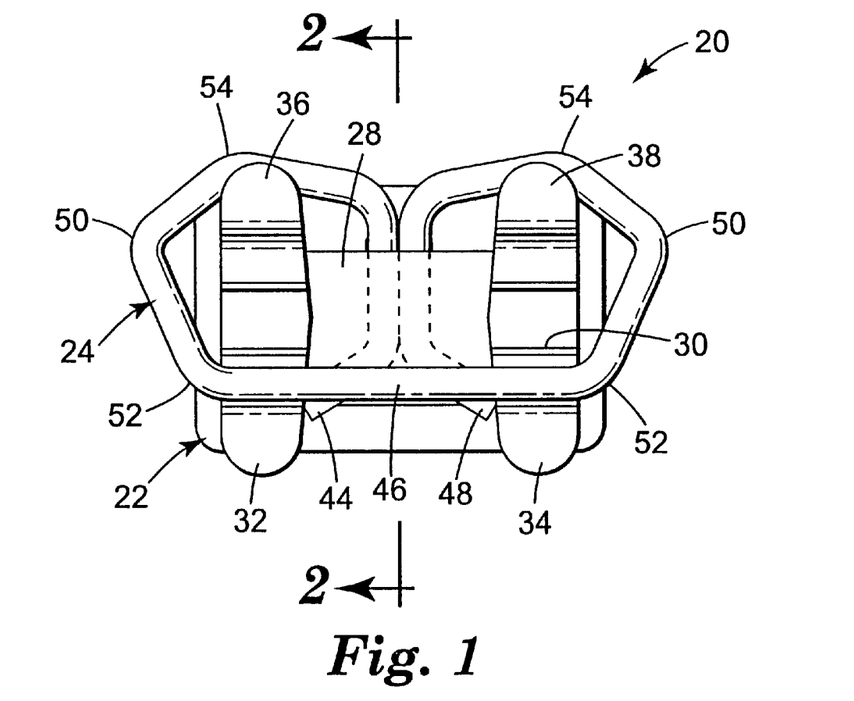
FIG. 1 is a front elevational view, looking in a lingual direction, of an orthodontic bracket assembly according to one embodiment of the invention, wherein a wire ligature latch and a bracket of the assembly are illustrated for exemplary purposes as they might appear before an archwire is received in an archwire slot of the bracket.
Figure 5:
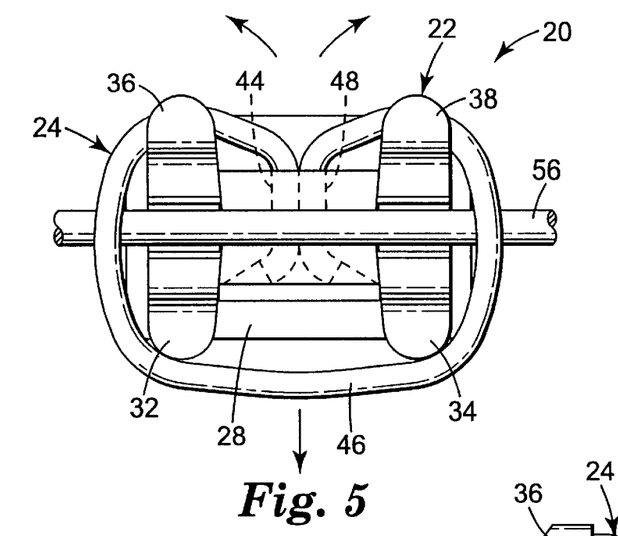
FIG. 5 is a front elevational view somewhat similar to FIG. 1 except that the ligature is shown as it appears at one point during movement toward a slot-closed position in order to retain the archwire in the archwire slot.

The first and third portions 44, 48 of the ligature 24 are received in side-by-side relationship in the passage 40 as illustrated, for example, in dashed lines in FIGS. 1 and 5. The first and third portions 44, 48 include outer end segments that are bent at an angle relative to the remaining segments of the portions 44, 48. The outer end segments extend away from each other in a generally mesial-distal direction and are somewhat inclined in an occlusal direction when the ligature 24 assumes the configuration shown in FIGS. 1 and 2. Each of the outer end segments of the portions 44, 48 slidingly engages a respective inclined wall section 42.

Figure 2:
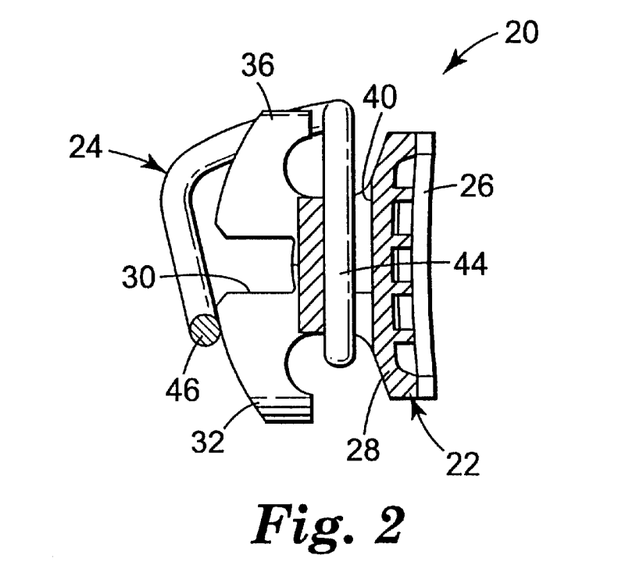
FIG. 2 is a side cross-sectional view of the assembly shown in FIG. 1 and taken along lines 2—2 of FIG. 1.

Operation and use of the assembly 20 will now be described. In FIGS. 1 and 2, the assembly is shown as it might appear before the onset of orthodontic therapy. In FIGS. 1 and 2, an occlusal section of the second ligature portion 46 is resting against a buccolabial surface of the occlusal tiewings 32, 34, while the first and third ligature portions 44, 48 are received in the passage 40. The ligature 24 has an inherent resilience when shaped such that the occlusal section of the second ligature portion 46 is biased against the occlusal tiewings 32, 34. Consequently, the ligature 24 does not appear loose or shift relative to the bracket 22 before use. The assembly 20 is shown in FIGS. 1 and 2 as it may appear before installation on a tooth, or after installation on a tooth but before receiving an archwire.

Figure 3:
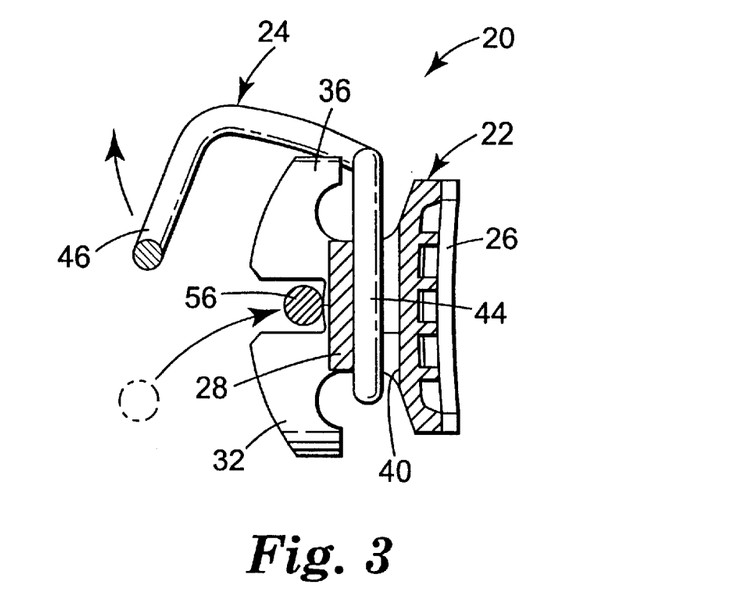
FIG. 3 is a view somewhat similar to FIG. 2 except that the ligature has been moved to a slot-open position in order to allow insertion of an archwire in the archwire slot.
Figure 4:
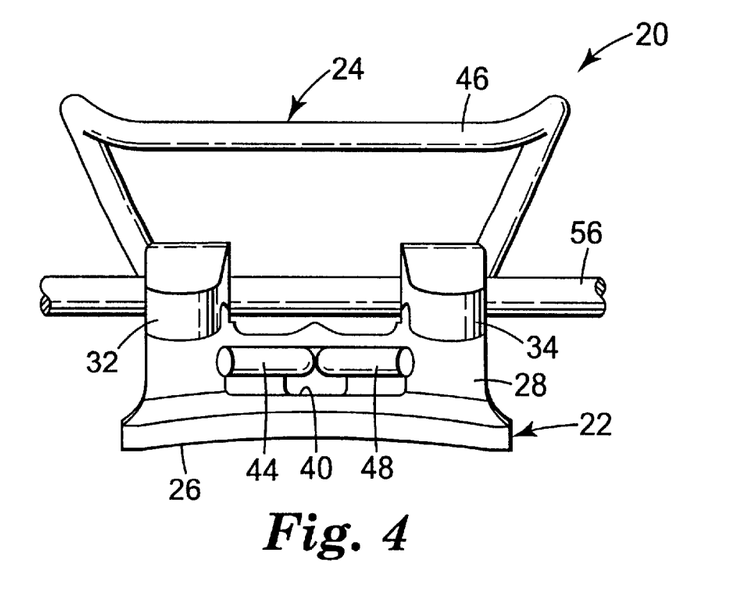
FIG. 4 is an end view, looking in a gingival direction, of the orthodontic bracket and ligature assembly shown in FIG. 3.

In FIGS. 3 and 4, the ligature 24 has been moved to a slot-open position so that an archwire 56 may be placed in the archwire slot 30. Typically, a fine-tipped dental tool such as a probe or explorer may be used to shift the second ligature portion 46 from its rest or idle position shown in FIGS. 1 and 2 to its slot-open position shown in FIGS. 3 and 4. When moving the ligature 24 to its slot-open position, the second ligature portion 46 is moved in a direction against its normal bias toward the gingival tiewings 36, 38 and swings in an arc relative to the first and third portions 44, 48 as shown by the arrow in FIG. 3.

Preferably, the second ligature portion 46 rests on an outer, gingival-most end section of the gingival tiewings 36, 38 when the ligature 24 is in its slot-open position as shown in FIGS. 3 and 4. In this manner, the ligature 24 remains in the configuration shown in FIGS. 3 and 4, and need not be held open by the hand instrument. Optionally, the outer end sections of the gingival tiewings 36, 38 have notches, shoulders or other structure engaging the second ligature portion 46 to assist in retaining the ligature 24 in a slot-open position. As another alternative, structure (such as a retention shoulder, flange or ledge) is provided adjacent the mesial side of the mesial-gingival tiewing 36 and adjacent the distal side of the distal-gingival tiewing 38 for engaging the second ligature portion 46 to facilitate retention of the ligature 24 in its slot-open position.

Figure 6:
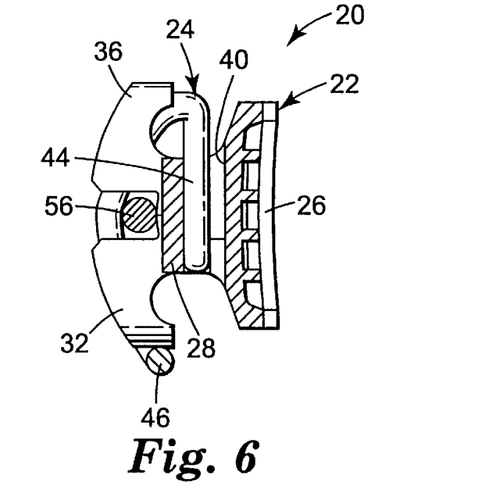
FIG. 6 is a view somewhat similar to FIGS. 2 and 3 except that the ligature is shown as it appears in FIG. 5.
Figure 7:
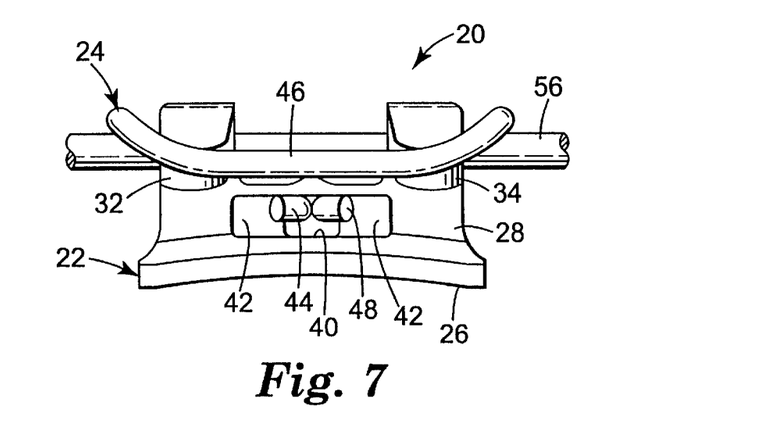
FIG. 7 is a view somewhat similar to FIG. 4 except that the ligature is shown as it appears in FIGS. 5 and 6.
Figure 8:
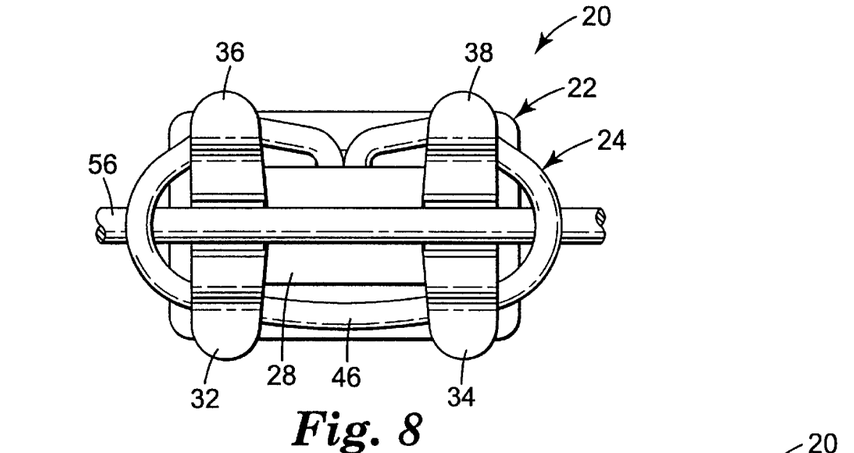
FIG. 8 is a view somewhat similar to FIGS. 1 and 5 except that the ligature is shown as it appears in its slot-closed position.
Figure 9:
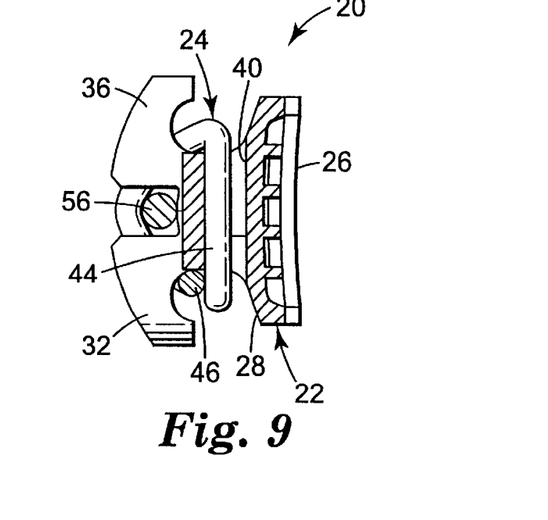
FIG. 9 is a view somewhat similar to FIGS. 2, 3 and 6 except that the ligature is shown as it appears in FIG. 8.
Figure 10:
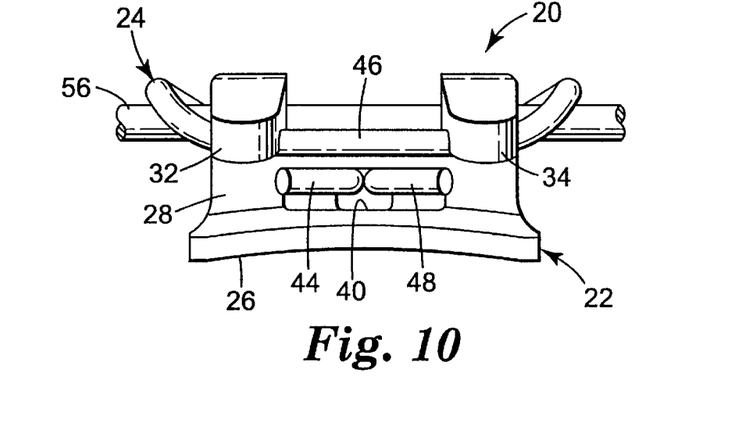
FIG. 10 is a view somewhat similar to FIGS. 4 and 7 except that the ligature is shown as it appears in its slot-closed position in FIGS. 8 and 9.

Once the archwire 56 is received in the archwire slot 30, the ligature 24 is moved from its slot-open position to its idle position as illustrated in FIGS. 1 and 2. Next, the ligature 24 is moved from its idle position to its slot-closed position as shown in FIGS. 8–10. As the ligature 24 is moved from its slot-open position to its slot-closed position, the second portion 46 swings in an arc relative to the first and third portions 44, 46. During movement of the ligature 24 from its idle position to its slot-closed position, a dental hand instrument such as a probe, explorer or other fine-tipped tool or a grasping tool such as a small-tipped pliers or tweezers is used to engage the central, occlusal section of the second ligature portion 46 and move that section past the outer occlusal end sections of the occlusal tie wings 32, 34 as shown in FIGS. 5–7. As another option, the practitioner's finger may be used to shift the ligature to its slot-closed position. During such closing movement, the practitioner may exert a small amount of force as may be necessary to pull the first and third ligature portions 44, 48 partially out of the passage 40 as needed in order to provide sufficient length for the second portion 46 to pass by the outer tips of the occlusal tiewings 32, 34.

Once the central, occlusal section of the second ligature portion 46 has been moved to a position lingually of the occlusal tiewings 32, 34, the second ligature portion 46 is released to enable the ligature 24 to snap to a slot-closed position. The inherent resiliency of the ligature 24 causes the ligature 24 to assume the configuration shown in FIGS. 8–10, where the central, occlusal section of the second ligature portion 46 is received in a tiewing undercut or notch located on a lingual side of the occlusal tiewings 32, 34. As the second ligature portion 46 is released, the resiliency and inherent bias of the ligature 24 will cause the first and third ligature portions 44, 48 to shift in an occlusal direction such that the outer end segments of the first and third ligature portions 44, 48 slide along the wall sections 42 in a mesial and distal direction respectively and also in an occlusal direction.

In the slot-closed orientation of the ligature 24 as shown in FIGS. 8–10, the archwire 56 is secured in the archwire slot 30 by the ligature 24. In particular, the second ligature portion 46 passes in a generally mesial-distal direction along a lingual side of the tiewings 32, 34, 36, 38, and also passes over a buccolabial side of the archwire 56 next to the mesial and distal sides of the bracket 22. Passage of the second ligature portion 46 along a lingual side of the bracket tiewings 32, 34, 36, 38 assures that the archwire 56 will remain in place in the archwire slot 30, even in instances where relatively large forces tending to separate the archwire 56 from the bracket 22 are present. The inherent bias of the ligature 24 toward its normal, relaxed configuration will tend to keep the ligature 24 in place and in the configuration shown in FIGS. 8–10 until such time as the practitioner wishes to move the ligature 24 to its slot-open position.

To open the archwire slot 30, the second ligature portion 46 is engaged by a hand instrument (such as the instruments mentioned above) and urged in an occlusal direction a distance sufficient to clear the outer tips of the occlusal tiewings 32, 34. During such occlusal movement, the first and third ligature portions 44, 48 may slide partially out of the passage 40. Next, the central occlusal section of the second ligature portion 46 is moved in a buccolabial direction until clear of the occlusal tiewings 32, 34. During such opening movement, a substantial part of the first and third ligature portions 44, 48 preferably remains in the passage 40, so that the ligature 24 does not separate from the bracket 22 unless otherwise desired.

The ligature 24 preferably has a circular cross-sectional shape, and optionally is a drawn wire made of a resilient material. One particularly preferred material for the ligature 24 is a metal alloy that exhibits superelastic characteristics, shape-memory characteristics or both. Examples of suitable materials include nickel-titanium alloys and beta-titanium alloys, as well as alloys that are clad or plated with an aesthetically pleasing material (such as a tooth-colored material). The superelastic, shape-memory alloys are advantageous because the ligature 24 can be bent through large deflections without taking a permanent set or change in shape from its pre-determined memory shape.

The superelastic, shape-memory alloys are also advantageous in that a relatively low yet constant force can be exerted on the archwire 56 by the ligature 24, assuring that the archwire 56 will tend to be fully seated in the archwire slot 30 in a lingual direction. The relatively low force exerted on the archwire 56 by the ligature 24 provides a relatively low coefficient of friction between the archwire 56 and the bracket 22, which may under certain circumstances provide a benefit by reducing the amount of total time needed to move the teeth to their intended locations.

Another benefit of making the ligature 24 of superelastic, shape-memory alloy materials is that the ligature 24 has greater flexibility than the clips and latches of many conventional self-ligating brackets. Oftentimes, the practitioner may choose to employ a relatively small archwire during the early course of treatment when using certain conventional self-ligating brackets because the relatively inflexible clips or latches of such brackets cannot be shifted sufficiently or closed, especially in instances where the teeth are located some distance from their intended final desired location. The assembly 20 of the invention is an advantage because the second ligature portion 46 can be shifted somewhat outwardly in a buccolabially direction as needed to pass over the labial side of the archwire 56 even when the latter is relatively large and/or is not fully seated in the archwire slot 30.

As another option, the ligature 24 is made of an aesthetically pleasing synthetic resinous material that is preferably translucent and colorless. A suitable material is ultra high molecular weight polyethylene such as is sold under the name "Spectra" by Allied Signal. These materials are particularly preferred where the bracket 22 is also made of an aesthetically pleasing material such as translucent polycarbonate or translucent or transparent ceramic materials such as monocrystalline or polycrystalline alumina. Such material could be a monofilament or a braided group of filaments, and tied in a knot once threaded through the passage 40 to retain it in place.

The bracket 22 may be made of any suitable material, including any one of the numerous materials known in the art for making orthodontic brackets. Examples of suitable materials include plastics (such as polycarbonate and glass fiber reinforced polycarbonate), ceramics (including transparent monocrystalline alumina and translucent polycrystalline alumina) and metals (such as type 300 stainless steels). Advantageously, conventional "vertical-slot" brackets may be used for the bracket 22, such that a specially-made bracket is unnecessary.

If desired, the ligature 24 may be easily removed from the bracket 22 by releasing and then lifting the central occlusal section of the second ligature portion 46 from its position shown in FIGS. 1 and 2 in a direction away from the occlusal tiewings 32, 34 and in a gingival direction, and then pulling the first and third ligature portions 44, 48 in a direction away from the body 28 until the portions 44, 48 are clear of the passage 40. The passage 40 can then be used for other applications, such as for receiving a hook or other auxiliary component as may be desirable during the course of treatment. During times when the ligature 24 is removed from the bracket 22, the bracket 22 may be ligated in a manner similar to conventional orthodontic brackets using elastomeric O-ring ligatures or wire strand ligatures around some or all of the tiewings 32, 34, 36, 38.

The bracket 22 and the ligature 24 may be sold and shipped to the practitioner assembled as shown in FIGS. 1 and 2, or may be sold as separate components. Optionally, the ligatures 24 may be sold alone and used with conventional "vertical-slot" brackets. During installation, a small pair of tweezers or pliers can be used to bend the outer end segments of the resilient first and third ligature portions 44, 48 to a straight orientation in order to place the latter into the passage 40 when desired. Such construction is an advantage over conventional self-ligating brackets having sliding clips that, when inadvertently broken or lost, require the bracket to be debonded from the tooth and replaced with another bracket.

A number of variations of the assembly 20 are possible. For example, brackets other than twin tiewing brackets may be used, such as single tiewing brackets having a single gingival tiewing and a single occlusal tiewing. Brackets with three tiewings can also be used, including brackets having a single occlusal tiewings and two spaced apart gingival tiewings. Brackets having archwire relief can also be used, including the "Uni-Twin" brand brackets and "Mini Uni-Twin" brand brackets from 3M Unitek as well as the brackets described in U.S. Pat. Nos. 4,531,911 and 5,857,850.

As other alternatives, the orientation of the ligature 24 may be reversed relative to the bracket 22 from that shown in the drawings and described above, such that the central section of the second ligature portion 46 is adjacent the gingival tiewings 36, 38 and the first and third ligature portions 44, 48 enter the passage 40 from an occlusal side of the body 28. In such an instance, the inclined wall sections 42 are preferably provided adjacent the gingival opening of the passage 40.

An orthodontic bracket assembly 20a according to another embodiment of the invention is illustrated in FIGS. 11–15 and includes a bracket 22a and a latch 24a. The bracket 22a has a base 26a as well as a body 28a that extends outwardly from the base 26a. The bracket 22a also includes an archwire slot 30a that extends through the body 28a in a generally mesial-distal direction. A rectangular archwire (shown in section) is illustrated in a seated position in the slot 30a in FIGS. 12–13 and 15 but is omitted in FIGS. 11 and 14.

Figures 11, 12, 13:
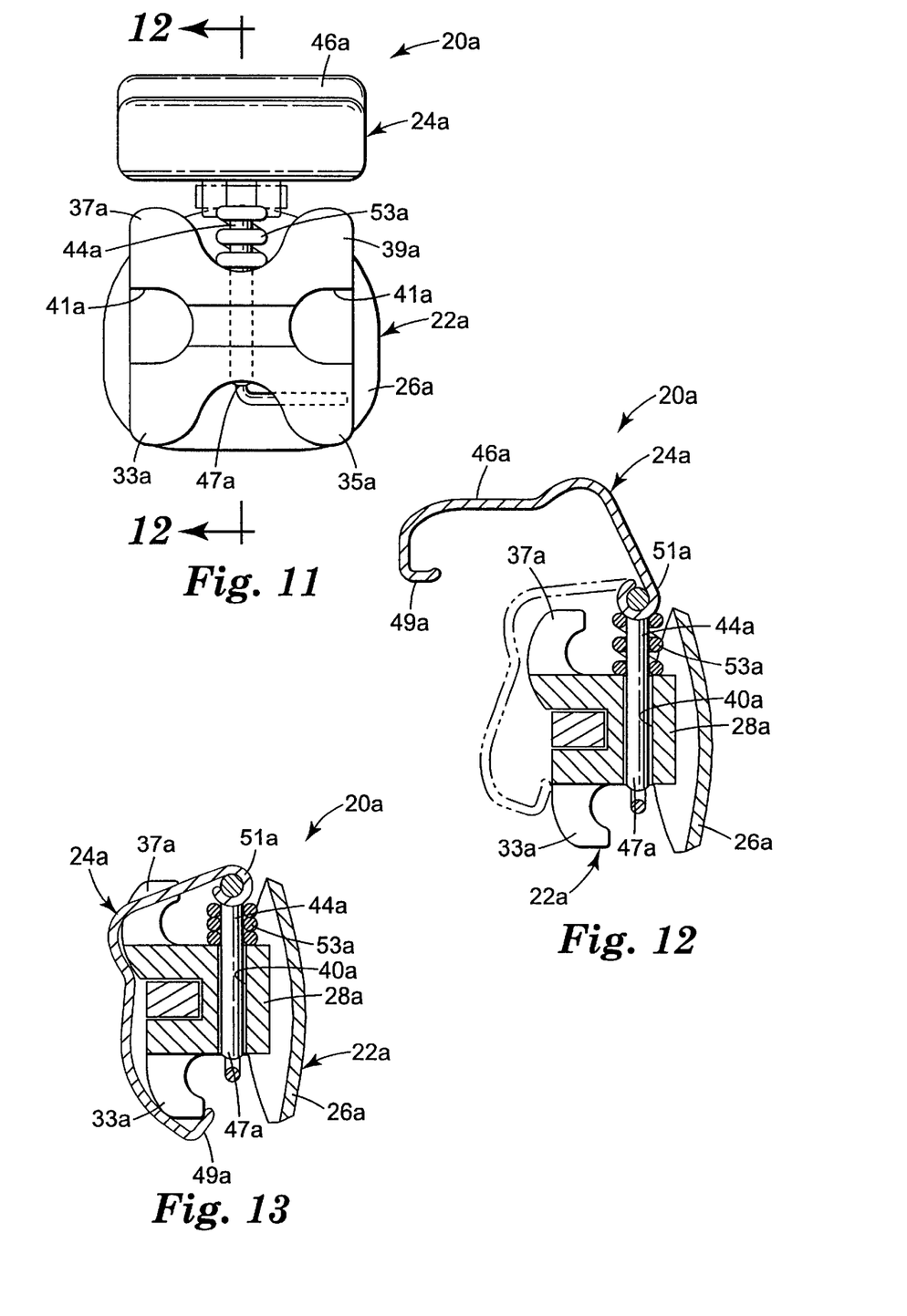
FIG. 11 is a front elevational view, looking in a lingual direction, of an orthodontic bracket assembly according to another embodiment of the invention, wherein a latch and a bracket of the assembly are somewhat different than the latch and bracket shown in FIGS. 1–10 and wherein the latch is depicted in a slot-open position to permit insertion of an archwire in an archwire slot of the bracket.
FIG. 12 is a side cross-sectional view of the assembly shown in FIG. 11 and taken along lines 12—12 of FIG. 11, and additionally showing the latch in dashed lines as it appears when moved to an idle position.
FIG. 13 is a view somewhat similar to FIG. 12 except that the latch is shown as it appears at one point during movement toward a slot-closed position.

The bracket 22a has an occlusal tiewing with a mesial-occlusal section 33a and a distal-occlusal section 35a. The bracket 22a also has a gingival tiewing with a mesial-gingival section 37a and a distal-gingival section 39a. The tiewing sections 33a, 37a together present a notch 41a that provides archwire relief in a manner similar to the archwire relief described in U.S. Pat. No. 4,531,911. A similar notch 41a is presented by the tiewing sections 35a, 39a.

The latch 24a includes a first portion 44a and a second portion 46a that is pivotally connected to the first portion 44a. The first portion 44a is received in a "vertical" passage 40a that is similar to the passage 40 described above. The first portion 44a includes an occlusal outer end segment 47a that is bent in an arc to extend in a generally mesial-distal direction in order to retain the first portion 44a in the passage 40a. The practitioner may straighten the outer end segment 47a of the first portion 44a to detach the latch 24a from the bracket 22a when desired. Preferably, and as shown, the outer end segment 47a has a smaller cross-sectional area in comparison to other regions of the first portion 44a in order to facilitate bending the segment 47a when desired.

As another option, the outer end segment 47a may be replaced with an enlarged head to retain the first portion 44a in the passage 40a. The enlarged head may be made by swaging or peening the occlusal end of the first portion 44a.

Figure 14:
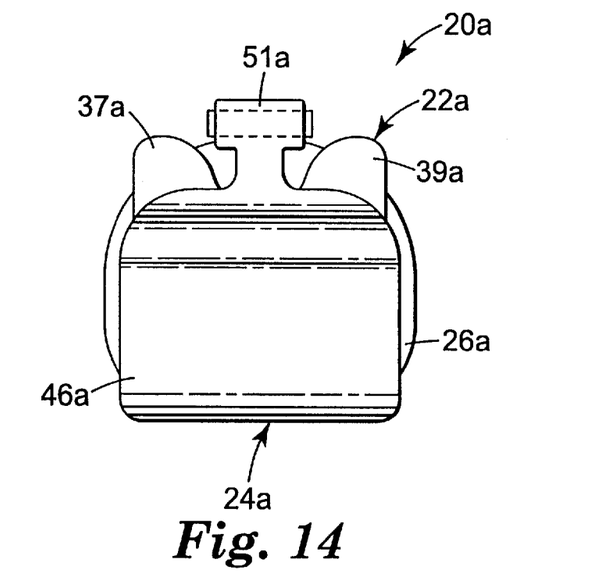
FIG. 14 is a view somewhat similar to FIG. 11 except that the latch is shown as it appears in its slot-closed position.
Figure 15:
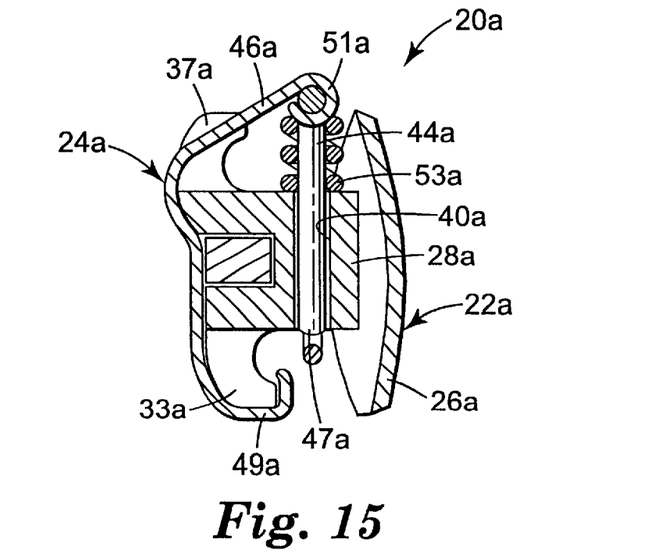
FIG. 15 is a view somewhat similar to FIG. 13 except that the latch is shown as it appears in FIG. 14 in its slot-closed position.

The second portion 46a of the latch 24a is in the nature of a formed, bent panel that preferably somewhat matches the configuration of underlying portions of the tiewing sections when the latch 24a is in its slot-closed position as shown in FIGS. 14 and 15. The latch 24a includes an occlusal end section 49a that extends past the occlusal ends as well as past a portion of the lingual side of the occlusal tiewing sections 33a, 35a when the latch 24a is in its slot-closed position. Optionally, the outer end section 49a has protrusions or other structure (not shown) that fits into mating recesses of the tiewing sections 33a, 35a to facilitate retaining the latch 24a in its slot-closed position.

A gingival end section 51a of the second latch portion 46a includes a pair of spaced apart cylindrical hinge members that extend about a mesial-distal pin connected to the occlusal end of the first latch portion 44a. The pin and the hinge members together function as a hinge to enable swinging, pivotal movement of the second latch portion 46a relative to the first latch portion 44a when desired. The hinge members and the pin enable latter movement of the second latch portion 46a in an arc about a generally mesial-distal reference axis that is aligned along the central axis of the pin in order to permit movement of the latch 24a between an idle position, a slot-open position and a slot-closed position as desired.

FIGS. 11 and 12 depict the latch 24a in its slot-open position. Preferably, the latch 24a is held in its slot-open position by friction between the hinge members and the pin mentioned in the preceding paragraph. FIG. 12 also depicts in dashed lines the location of the latch 24a when in a rest or idle position.

To close the latch 24a, the latch 24a is initially moved from its slot-open position to its idle position, and then moved toward the orientation shown in FIG. 13. During such latter movement, the first latch portion 44a is moved in an occlusal direction against the bias of a spring 53a that is located between the pin and the gingival side of the bracket body. Moving of the first latch portion 44a in an occlusal direction enables the occlusal end section 49a of the second latch portion 46a to extend around the occlusal end of the occlusal tiewing sections 33a, 35a in the manner shown in FIG. 13. The latch 24a can be closed by finger pressure or by the use of a suitable hand instrument.

FIGS. 14 and 15 illustrate the position of the latch 24a in its slot-closed position. Once the occlusal end section 49a is shifted to a position past the occlusal-lingual edge of the occlusal tiewing sections 33a, 35a, finger pressure or the pressure of a hand instrument upon the latch 24a is released and the spring 53a urges the second latch portion 46a in a gingival direction. Movement of the second latch portion 46a in a gingival direction enables the occlusal end section 49a to snap in place around the occlusal ends of the tiewing sections 33a, 35a and thereafter retain the latch 24a in its slot-closed position.

The second latch portion 46a is somewhat resilient to facilitate movement of the latch 24a and closing the latch 24a when desired. Optionally, the latch 24a is made of a superelastic, shape memory alloy as described above in connection with the latch 24. To open the latch 24a, the occlusal end section 49a is grasped by a suitable hand instrument such as a dental probe or explorer, and moved about the occlusal-lingual edge of the occlusal tiewing sections 33a, 35a. During such movement, the first latch portion 44a is shifted in an occlusal direction as needed against the bias of the spring 53a.

Figure 16:
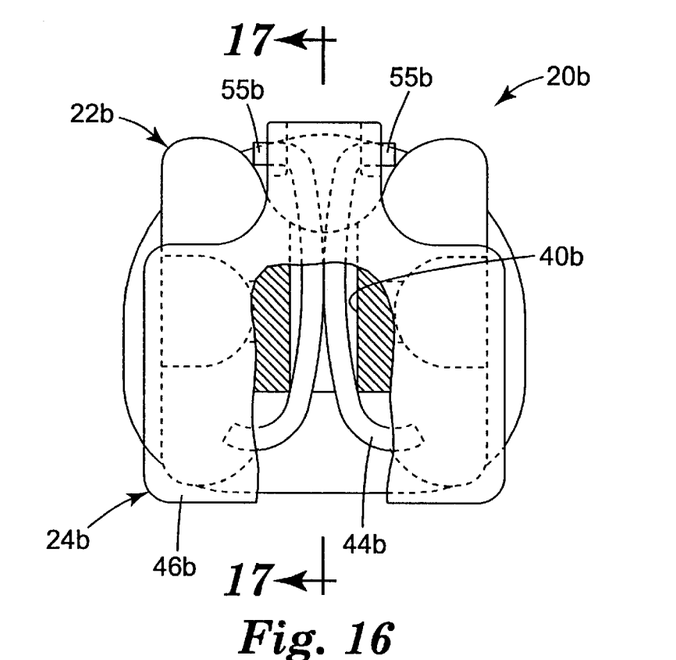
FIG. 16 is a front elevational view in partial section, looking in a lingual direction, of an orthodontic bracket assembly according to yet another embodiment of the invention, wherein a latch of the assembly is illustrated for exemplary purposes as it appears in its slot-closed position.
Figure 17:
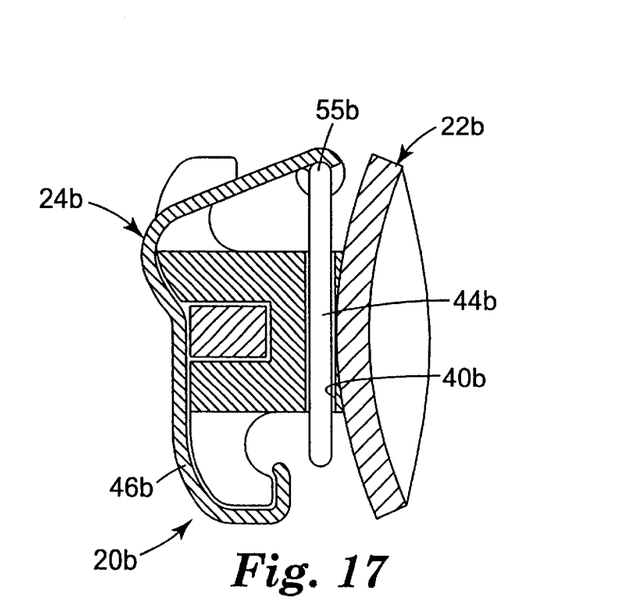
FIG. 17 is a side cross-sectional view of the assembly shown in FIG. 16 and taken along lines 17—17 of FIG. 16.

An orthodontic bracket assembly 20b according to another embodiment of the invention is illustrated in FIGS. 16 and 17. The assembly 20b is essentially the same as the assembly 20a described above, except for the aspects described in the following paragraphs.

The assembly 20b includes a latch 24b with a first latch portion 44b that is received in a "vertical" passage 40b of a bracket 22b. The bracket 22b is essentially the same as the bracket 22a, except that the passage 40b is optionally somewhat larger in cross-sectional area than the passage 40 as may be needed to accommodate the cross-sectional area of the first latch portion 44b.

The first latch portion 44b comprises a pair of legs 55b having a somewhat "U"-shaped configuration. The legs 55b have gingival portion that extend in opposite directions along a generally mesial-distal reference axis. The legs 55b also have curved occlusal portions that extend in opposite directions away from each other at a location that is near the occlusal entrance of the passage 40b.

A second latch portion 46b is somewhat similar to the second latch portion 46a, except that the second portion 46b includes a pair of hinge members that extend about the gingival portions of the legs 55b. The hinge members and the gingival portions of the legs 55b cooperate to function as a hinge to enable pivotal movement of the second latch portion 46b relative to the first latch portion 44b when desired.

Preferably, the first latch portion 44b is resilient. When desired, the practitioner may disconnect the latch 24b from the bracket 22b by opening the latch 24b and then pulling the first latch portion 44b in a gingival direction in order to deform the occlusal portions of the legs 55b to a somewhat straight orientation parallel to the passage 40b so that the legs 55b can then be pulled free of the passage 40b. Optionally, the practitioner may use a small-tipped pliers or other hand instrument in order to bend the occlusal portions of the legs 55b to a straightened, parallel orientation to facilitate removal of the legs 55b from the passage 40b. The latch 24b may be reconnected to the bracket 22b when desired by straightening the occlusal portions of the legs 55b for reentry into the passage 40b.

Figure 18:
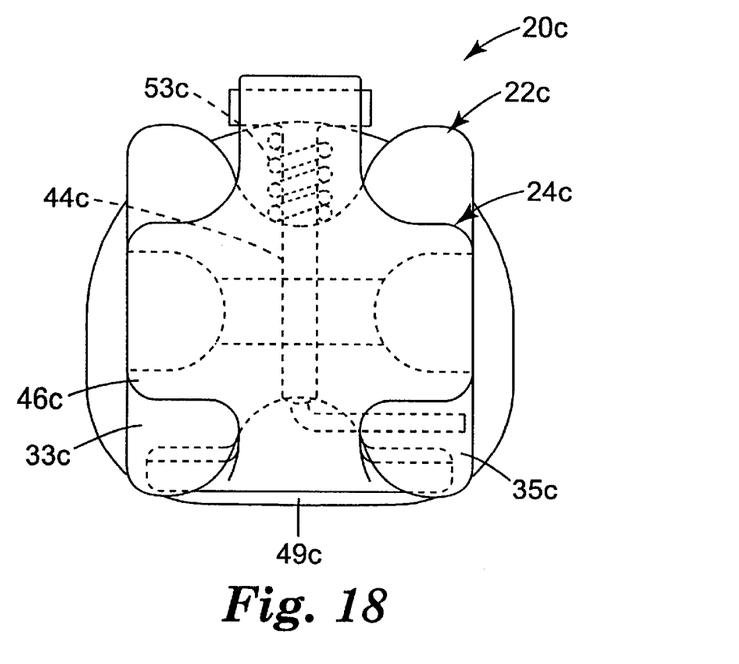
FIG. 18 is a front elevational view, looking in a lingual direction, of a bracket assembly that is constructed according to another embodiment of the invention, and illustrating a latch of the assembly in a slot-closed position.
Figure 19:
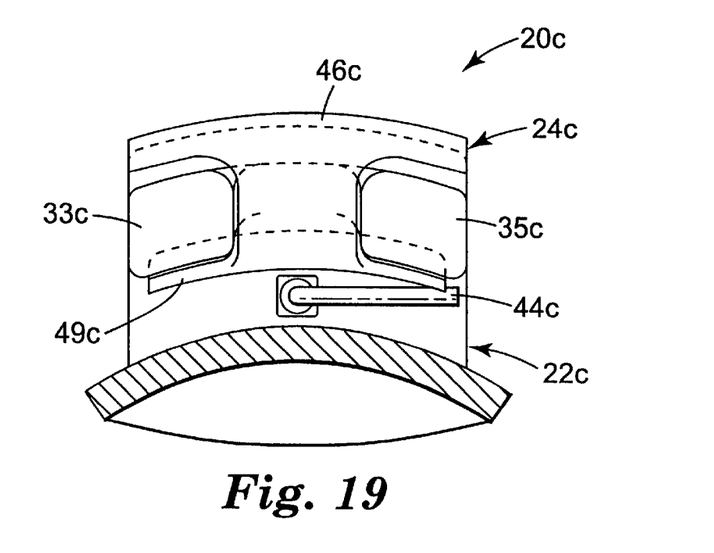
FIG. 19 is an end view looking in a gingival direction of the assembly shown in FIG. 18.

An orthodontic bracket assembly 20c according to a further embodiment of the invention is illustrated in FIGS. 18 and 19. The assembly 20c includes a bracket 22c that is the same as the bracket 22a described above. The assembly 20c also includes a latch 24c that is somewhat similar to the latch 24a, except for the aspects that are described below.

The latch 24c includes a first portion 44c and a second portion 46c that is pivotally connected to the first portion 44c. The first latch portion 44c is identical to the first latch portion 44a, but the second latch portion 46c is somewhat different than the second latch portion 46a. As shown in FIG. 18, the second latch portion 46c has a middle region that extends across an archwire slot of the bracket 22c as well as notches (similar to notches 41a) that provide archwire relief. However, outer corners of the tiewings are not covered by the second latch portion 46c when closed.

An occlusal end section 49c of the latch 24c has a somewhat "T"-shaped configuration, with a region that extends between a mesial-occlusal tiewing section 33c and a distal-occlusal tiewing section 35c in a lingual direction when the latch 24c is closed. An outer end region of the occlusal end latch section 49c extends along a lingual side of the tiewing sections 33c, 35c in opposite directions along a generally mesial-distal reference axis when the latch 24c is closed.

As shown in FIGS. 18 and 19, the tiewing sections 33c, 35c provide a secure stop for retaining the latch 24c in a slot-closed position. To open the latch 24c, the latch 24c is moved in an occlusal direction against the bias of a spring 53c until the occlusal end section 49c of the second latch portion 46c is clear of the tiewing sections 33c, 35c. The second latch portion 46c can then be swung in an arc to a slot-open position similar to that shown in FIG. 12.

Those skilled in the art will recognize that a number of other modifications to the invention are also possible. Accordingly, the invention should not be deemed limited to the specific embodiments described above and illustrated in the drawings, but instead only by a fair scope of the claims that follow along with their equivalents.

What is claimed is:

1. An orthodontic bracket assembly comprising:
   an orthodontic bracket having a base, a body extending from the base and an archwire slot extending in a generally mesial-distal direction, the body having an occlusal side and a gingival side, the bracket also including at least one gingival tiewing located gingivally of the gingival side, at least one occlusal tiewing located occlusally of the occlusal side and a passage extending in a generally occlusal-gingival direction; and
   a latch having a first portion and second portion, wherein the second portion is movable between a slot-closed position for retaining an archwire in the archwire slot and a slot-open position for removal or insertion of an archwire in the archwire slot, wherein the second portion is connected to the first portion adjacent one of the occlusal side and the gingival side, wherein the second portion engages the lingual side of at least one of the tiewings adjacent the other of the occlusal side and the gingival side when the second portion is in the slot-closed position and is released from such engagement when the second portion is in the slot-open position, and wherein the first portion is received in the passage.

2. An orthodontic bracket assembly according to claim 1 wherein the first portion is movable in the passage in a direction along a generally occlusal-gingival reference axis as the second portion is moved between the slot-open position and the slot-closed position.

3. An orthodontic bracket assembly according to claim 1 wherein the latch is a wire ligature.

4. An orthodontic bracket assembly according to claim 3 wherein the ligature extends lingually of all of the tiewings when the second portion is in the slot-closed position.

5. An orthodontic bracket assembly according to claim 3 wherein the tiewings each include an outer end section, and wherein the second portion rests on the outer end section of at least one tiewing when the second portion is in the slot-open position.

6. An orthodontic bracket assembly according to claim 3 wherein the ligature includes a third portion, wherein the second portion is located between the third portion and the first portion in directions along the length of the ligature, and wherein the third portion is received in the passage in side-by-side relation to the first portion.

7. An orthodontic bracket assembly according to claim 6 wherein the first portion and the third portion each include outer end segments that extend away from each other in generally mesial-distal directions.

8. An orthodontic bracket assembly according to claim 7 wherein the body includes a pair of wall sections that extend at an angle relative to an occlusal-gingival reference axis and that converge toward each other adjacent the passage, and wherein each of the outer end segments of the ligature slidingly engage a respective wall section.

9. An orthodontic bracket assembly according to claim 7 wherein the first portion and the third portion slide together in the passage in a direction along a generally occlusal-gingival reference axis as the second portion is moved from a slot-open position to a slot-closed position.

10. An orthodontic bracket assembly according to claim 1 wherein the body includes a central reference axis that extends in a generally occlusal-gingival direction, and wherein the passage extends along the central reference axis.

11. An orthodontic bracket assembly according to claim 10 wherein the passage is located lingually of the archwire slot.

12. An orthodontic bracket assembly according to claim 1 wherein the latch is resilient.

13. An orthodontic bracket assembly according to claim 12 wherein the latch is made of a shape-memory alloy.

14. An orthodontic bracket assembly according to claim 13 wherein the alloy is selected from a group consisting of nickel-titanium and beta-titanium.

15. An orthodontic bracket assembly according to claim 1 wherein the passage extends through the body in a location adjacent the base.

16. An orthodontic bracket assembly according to claim 1 wherein the first portion is releasably received in the passage.

17. An orthodontic bracket assembly according to claim 1 wherein the second portion has a generally open-loop configuration when viewed in a lingual direction.

18. An orthodontic bracket assembly according to claim 1 wherein the second portion also extends labially across at least one of the tiewings when the second portion is in the slot-closed position.

19. An orthodontic bracket assembly according to claim 18 wherein the second portion extends labially across a majority of each tiewing when the second portion is in the slot-closed position.

20. An orthodontic bracket assembly according to claim 18 including a spring for biasing the first portion in a certain direction relative to the body.

21. An orthodontic bracket assembly comprising:
   an orthodontic bracket having a base, a body extending from the base and an archwire slot extending in a generally mesial-distal direction, the bracket also including a mesial-gingival tiewing, a mesial-occlusal tiewing, a distal-gingival tiewing and a distal-occlusal tiewing, the bracket also including a passage extending along a generally occlusal-gingival reference axis; and
   a wire ligature having a first portion, a second portion and a third portion, wherein the second portion is located between the first portion and the third portion in directions along the length of the ligature, wherein the second portion is movable between a slot-closed position for retaining an archwire in the archwire slot and a slot-open position for removal or insertion of an archwire in the archwire slot, wherein the second portion extends lingually past each of the tiewings when the second portion is in the slot-closed position and wherein the first portion and the third portion are received in the passage.

22. An orthodontic bracket assembly according to claim 21 wherein the first portion and the third portion move together in the passage in directions along a generally occlusal-gingival reference axis as the second portion is moved from a slot-closed position to a slot-open position.

23. An orthodontic bracket assembly according to claim 21 wherein the passage is located lingually of the archwire slot.

24. An orthodontic bracket assembly according to claim 21 wherein the ligature extends lingually of each tiewing when the second portion is in the slot-closed position.

25. An orthodontic bracket assembly according to claim 21 wherein the tiewings each include an outer end section, and wherein the second portion rests on the outer end section of at least one tiewing when the second portion is in the slot-open position.

26. An orthodontic bracket assembly according to claim 21 wherein the first portion and the third portion each include outer end segments that extend away from each other in generally mesial-distal directions.

27. An orthodontic bracket assembly according to claim 26 wherein the body includes a pair of wall sections that extend at an angle relative to an occlusal-gingival reference axis and that converge toward each other adjacent the passage, and wherein each of the outer end segments of the ligature slidingly engage a respective wall section.

28. An orthodontic bracket assembly according to claim 21 wherein each tiewing extends in a direction away from the archwire slot at a certain angle relative to the length of the archwire slot, and wherein the passage has a central axis that extends parallel to the direction of extension of the tiewings.

29. An orthodontic bracket assembly according to claim 21 wherein the ligature is made of a shape-memory alloy.

30. An orthodontic bracket assembly according to claim 21 wherein the first portion is releasably received in the passage.

31. An orthodontic bracket assembly comprising:
   an orthodontic bracket having a base, a body extending from the base and an archwire slot extending in a generally mesial-distal direction, the bracket also including at least one gingival tiewing and at least one occlusal tiewing, each occlusal tiewing having an outer end section facing in a generally occlusal direction, each gingival tiewing having an outer end section facing in a generally gingival direction, the bracket also including a passage extending along a generally occlusal-gingival reference axis; and
   a latch having a first portion and a second portion, wherein the first portion is coupled to the body, wherein the second portion is movable between a slot-closed position for retaining an archwire in the archwire slot and a slot-open position for removal or insertion of an archwire in the archwire slot, wherein the second portion extends lingually past each of the tiewings when the second portion is in the slot-closed position, wherein the second portion rests on the outer end section of at least one tiewing when the second portion is in the slot-open position, wherein the first portion is movable in the passage in a direction along a generally occlusal-gingival reference axis as the second portion is moved between the slot-open position and the slot-closed position in order to help retain the second portion in the slot-open position.

32. An orthodontic bracket assembly according to claim 31 wherein the latch extends lingually of all of the tiewings when the second portion is in the slot-closed position.

33. An orthodontic bracket assembly according to claim 31 wherein the body includes a central reference axis that extends in a generally occlusal-gingival direction, and wherein the passage extends along the central reference axis.

34. An orthodontic bracket assembly according to claim 31 wherein the latch is made of a shape-memory alloy.

35. An orthodontic bracket assembly according to claim 31 wherein the passage is located lingually of the archwire slot.

36. An orthodontic bracket assembly comprising:
   an orthodontic bracket having a base, a body extending from the base and an archwire slot extending in a generally mesial-distal direction, the bracket also including at least one gingival tiewing and at least one occlusal tiewing, each occlusal tiewing having an outer end section facing in a generally occlusal direction, each gingival tiewing having an outer end section facing in a generally gingival direction, the bracket also including a passage extending along a generally occlusal-gingival reference axis; and
   a latch having a first portion and second portion, wherein the first portion is coupled to the body, wherein the second portion is movable between a slot-closed position for retaining an archwire in the archwire slot and a slot-open position for removal or insertion of an archwire in the archwire slot, wherein the second portion extends lingually past each of the tiewings when the second portion is in the slot closed position, wherein the second portion rests on the outer end section of at least one tiewing when the second portion is in the slot-open position in order to help retain the second portion in the slot-open position, wherein the latch comprises a wire ligature that includes a third portion, wherein the second portion is located between the third portion ant the first portion in directions along the length of the latch, and wherein the third portion is received in the passage in side-by-side relation to the first portion.

37. An orthodontic bracket assembly according to claim 36, wherein the first portion and the third portion each include outer end segments that extend away from each other in generally mesial-distal directions.

38. An orthodontic bracket assembly according to claim 37 wherein the body includes a pair of wall sections that extend at an angle relative to an occlusal-gingival reference axis and that converge toward each other adjacent the passage, and wherein each of the outer end segments of the ligature slidingly engage a respective wall section.

39. An orthodontic bracket assembly according to claim 37 wherein the first portion and the third portion slide together in the passage in a direction along a generally occlusal-gingival reference axis as the second portion is moved from a slot-open position to a slot-closed position.

* * * * *

UNITED STATES PATENT AND TRADEMARK OFFICE
CERTIFICATE OF CORRECTION

PATENT NO. : 6,325,622 B1
DATED : December 4, 2001
INVENTOR(S) : John S. Kelly et al.

It is certified that error appears in the above-identified patent and that said Letters Patent is hereby corrected as shown below:

<u>Column 16,</u>
Line 34, "ant" should read -- and --.

Signed and Sealed this

Seventh Day of May, 2002

*Attest:*

JAMES E. ROGAN
*Director of the United States Patent and Trademark Office*

*Attesting Officer*